United States Patent
Pickert et al.

(10) Patent No.: US 10,509,137 B2
(45) Date of Patent: Dec. 17, 2019

(54) MONITORING METHOD AND MONITORING SYSTEM

(71) Applicant: Siemens Healthcare GmbH, Erlangen (DE)

(72) Inventors: Nils Pickert, Erlangen (DE); Markus Weingarten, Bamberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/059,502

(22) Filed: Aug. 9, 2018

(65) Prior Publication Data
US 2019/0049604 A1 Feb. 14, 2019

(30) Foreign Application Priority Data

Aug. 10, 2017 (EP) ..................................... 17185687

(51) Int. Cl.
*G01T 1/29* (2006.01)
*A61B 6/00* (2006.01)
(Continued)

(52) U.S. Cl.
CPC ............ *G01T 1/2964* (2013.01); *A61B 6/107* (2013.01); *A61B 6/461* (2013.01); *A61B 6/54* (2013.01);
(Continued)

(58) Field of Classification Search
CPC ......... G01T 1/2964; G01T 1/02; A61B 6/107; A61B 6/461; A61B 6/54; A61B 6/58; G06N 3/02
(Continued)

(56) References Cited

U.S. PATENT DOCUMENTS 6,272,368 B1* 8/2001 Alexandrescu .......... A61B 6/08
250/349
6,435,717 B1* 8/2002 Kohler ................... A61B 6/107
378/205
(Continued)

FOREIGN PATENT DOCUMENTS

CN 104582580 A 4/2015
WO WO2015132069 A1 9/2015
WO WO2015162101 A1 10/2015

OTHER PUBLICATIONS

European Communication Under Rule 73(3) EPC for corresponding Application No. 17185687.5-1124 dated Mar. 27, 2019, with English translation.
(Continued)

*Primary Examiner* — Taeho Jo
(74) *Attorney, Agent, or Firm* — Lempia Summerfield Katz LLC

(57) ABSTRACT

A method is provided for monitoring the exposure to radiation of medical personnel during an X-ray examination of an examination object with an X-ray apparatus. A monitoring unit is activated and continuously scans a first three-dimensional volume that includes a region directly irradiated by the X-ray beam, for objects. When an object is detected, automatic evaluation is performed as to whether the object is a human body part that does not correspond to the examination object and a signal or a display is output if a human body part is determined inside the three-dimensional volume that does not correspond to the examination object.

18 Claims, 3 Drawing Sheets

(51) Int. Cl.
  *G01T 1/02* (2006.01)
  *G06N 3/02* (2006.01)
  *A61B 6/10* (2006.01)
(52) U.S. Cl.
  CPC .................. *A61B 6/58* (2013.01); *G01T 1/02* (2013.01); *G06N 3/02* (2013.01)
(58) Field of Classification Search
  USPC ........................................................ 378/146
  See application file for complete search history.

(56) References Cited

U.S. PATENT DOCUMENTS

| | | | | |
|---|---|---|---|---|
| 2005/0226382 | A1* | 10/2005 | Eck | A61B 6/583 378/117 |
| 2008/0101538 | A1* | 5/2008 | Schliermann | A61B 6/08 378/95 |
| 2011/0037840 | A1 | 2/2011 | Hiltl et al. | |
| 2011/0060423 | A1* | 3/2011 | Bonfiglio | A61B 6/00 700/11 |
| 2011/0317815 | A1 | 12/2011 | Bernhardt et al. | |
| 2012/0187312 | A1* | 7/2012 | Guez | A44C 5/20 250/492.1 |
| 2012/0236996 | A1* | 9/2012 | Guez | A44C 5/20 378/117 |
| 2013/0301797 | A1* | 11/2013 | Guez | A44C 5/20 378/51 |
| 2014/0294146 | A1* | 10/2014 | Guez | A44C 5/20 378/51 |
| 2015/0245804 | A1 | 9/2015 | Kieft | |
| 2015/0272520 | A1* | 10/2015 | Kobayashi | A61B 6/06 378/62 |
| 2015/0313568 | A1* | 11/2015 | Guez | A44C 5/20 378/151 |
| 2015/0327824 | A1* | 11/2015 | Kleinszig | G09G 3/2003 378/62 |
| 2016/0206274 | A1 | 7/2016 | Kang et al. | |
| 2017/0071558 | A1* | 3/2017 | Hoornaert | A61B 6/06 |
| 2017/0209110 | A1* | 7/2017 | Kiraly | A61B 6/0407 |

OTHER PUBLICATIONS

European Search Report for corresponding Application No. 17185687.5-1124, dated Apr. 13, 2018, with English translation.
European Search Report for corresponding Application No. 17185687.5-1124, dated Feb. 1, 2018, with English translation.
European Search Report for corresponding Application No. 17185687.5-1124, dated Apr. 13, 2018.
European Search Report for corresponding Application No. 17185687.5-1124, dated Feb. 1, 2018.
Chinese Office Action for Chinese Application No. 201810900912.2 dated Jul. 1, 2019, with English translation.

* cited by examiner

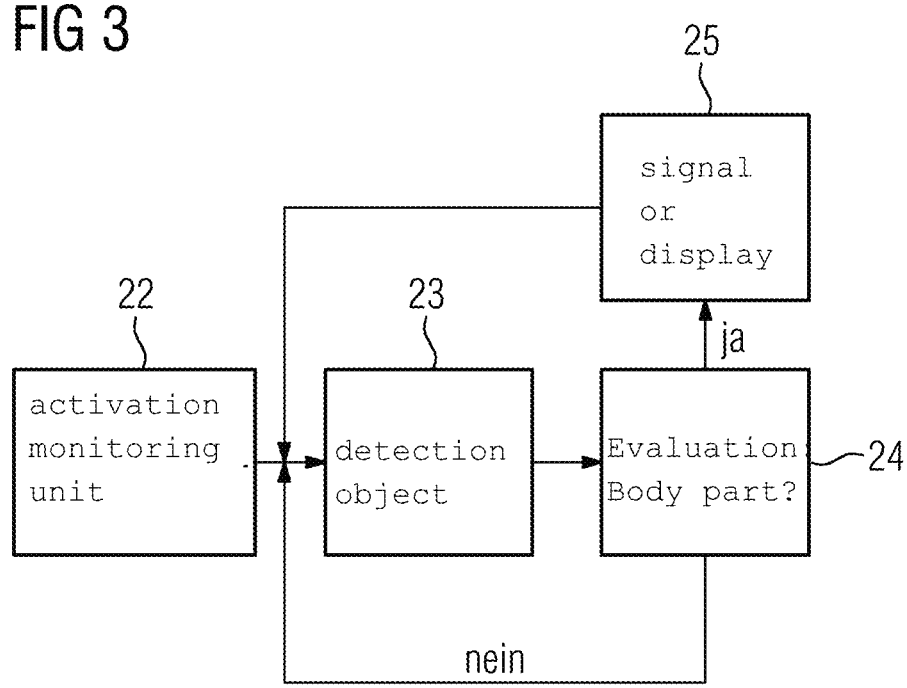

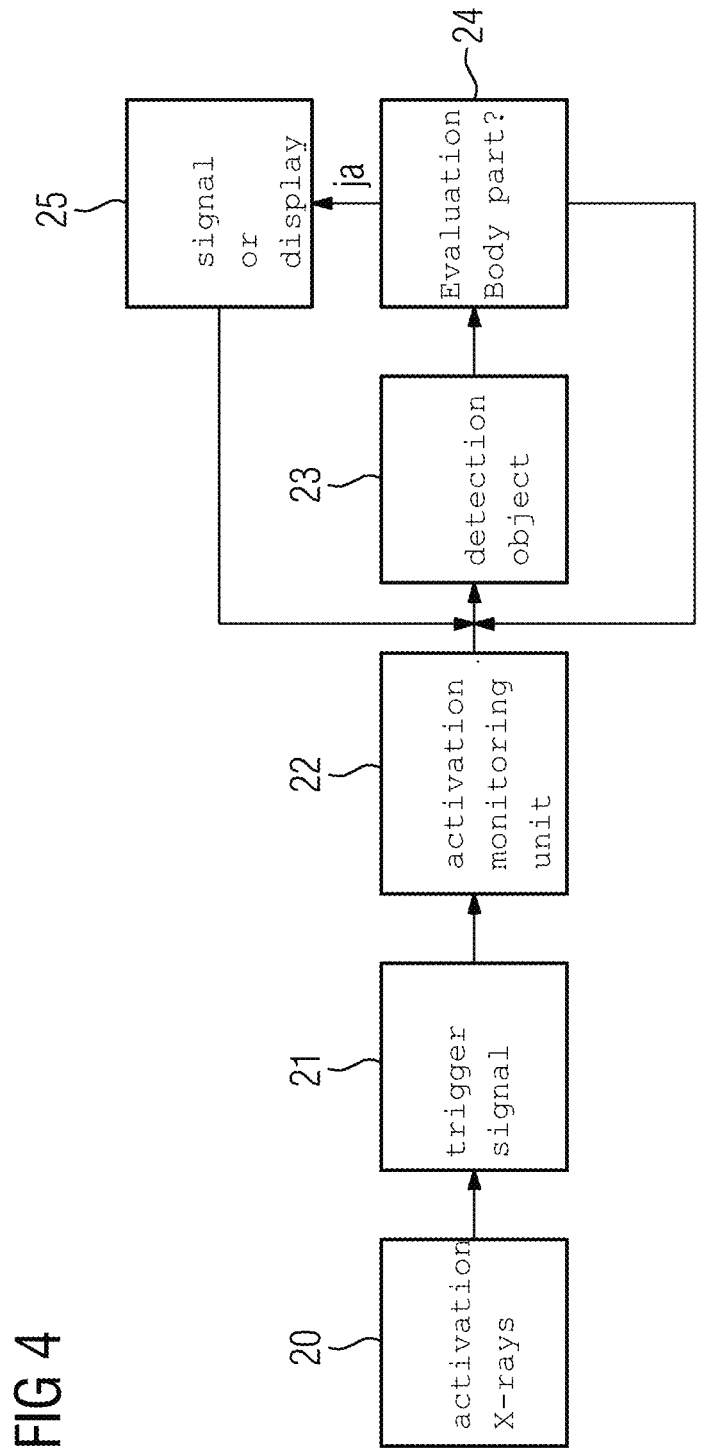

MONITORING METHOD AND MONITORING SYSTEM

CROSS REFERENCE TO RELATED APPLICATIONS

This application claims the benefit of EP17185687.5 filed on Aug. 10, 2017, which is hereby incorporated by reference in its entirety.

FIELD

Embodiments relate to a method for monitoring the exposure to radiation of medical personnel.

BACKGROUND

For medical personnel that operate in the environment of medical imaging equipment emitting X-ray radiation, it is difficult to accurately estimate where exactly direct X-ray radiation or even scatter radiation is located. As such, body parts, for example, arms and hands, of medical personnel are unintentionally located in the beam path or in zones affected by scatter radiation. This may occur frequently in the field of interventional and surgical procedures under X-ray radiation, where the hands of doctors are positioned close to the patient/examination object during the operation. Direct X-ray radiation creates a significant health risk for the people affected, primarily if the radiation occurs over a relatively long period; scatter radiation, for example due to scattering on equipment or the patient, also constitutes a risk. Furthermore, additional scatter radiation is generated by the body parts in the direct beam path and also adversely affects imaging. Overall, it is desirable to increase awareness of the danger and to reduce the danger of undesirable exposure to radiation as a whole.

SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a method for monitoring medical personnel, that provides reliable indication of undesirable exposure to radiation.

An embodiment provides a method for monitoring the exposure to radiation of medical personnel during an X-ray examination of an examination object with an X-ray apparatus including the following steps: activation of a monitoring unit, where the monitoring unit continuously scans a first three-dimensional volume, that includes a region that may be directly irradiated and/or is irradiated by the X-ray beam, for objects, in the event of detection of an object, automatic evaluation as to whether the object is a human body part that does not correspond to the examination object, and outputting a signal or a display if a human body part is determined inside the three-dimensional volume that does not correspond to the examination object. By way of the method there is continuous monitoring during the application of X-ray radiation as to whether a human body part of medical personnel is located in the beam path, and as soon as such a body part is discovered an indication of the danger is immediately given. As a result, the medical personnel are immediately made aware of the danger and the affected person may instantly remove his body part from the danger.

The method increases threat awareness and significantly reduces the health risk for medical personnel as the duration of exposure to radiation may be reduced.

According to an embodiment, the first three-dimensional volume is automatically specified as a function of the beam path of the X-ray. For example, information about the beam path (for example collimation, etc.) may be passed to the monitoring unit. Information about the region irradiated by the X-ray beam is continuously renewed and the first three-dimensional volume adjusted accordingly for timely monitoring.

According to an embodiment, the monitoring unit is formed by at least one 3D camera or an infrared device or a terahertz camera. Such devices may be well suited to comprehensive monitoring of 3-dimensional space sections. Other monitoring equipment may also be used in addition or as an alternative.

According to an embodiment, the evaluation is carried out by a computer vision method. For example, an object recognition or object classification method may be used. Neural networks may be used for the automatic evaluation.

According to an embodiment, in the event of determination of a human body part inside the first three-dimensional volume that does not correspond to the examination object, an adjustment of the collimation of the X-ray beam of the X-ray source is carried out to reduce the danger to the person whose body part is located in the beam path. The collimation changes the region irradiated by the X-ray beam in such a way that the human body part is no longer irradiated or is irradiated with a lower dose. Therefore, for example what is known as a finger filter may be automatically pushed into the beam path, and this seals off the body part from the radiation.

According to an embodiment, the monitoring unit also scans a second three-dimensional volume, that includes a region affected by scatter radiation, for objects. Whether the object is a human body part that does not correspond to the examination object is determined, and a signal or a display is output if a human body part is determined inside the second three-dimensional volume that does not correspond to the examination object. In this way, the medical personnel can also point toward a dangerous situation in respect of the scatter radiation and therefore the risk is reduced further.

Activation of the monitoring unit is triggered by the activation of an X-ray source that emits an X-ray beam. Alternatively, continuous monitoring, or monitoring extending at least over a relatively long period, may also be provided as the X-ray radiation application, however. A volume potentially affected by X-ray radiation may also be scanned for objects and evaluated during a period without X-ray radiation. If a body part is determined, that is located in the beam path during activation of the X-ray source, then a signal/display may likewise be output.

According to an embodiment, the signal is formed by an optical or acoustic or haptic signal. Therefore, for example, a piercingly loud acoustic signal may be emitted, or a warning light may flash, or a vibrating alarm may be triggered. Appropriately striking colors and/or sounds may be used here. A display may also appear on a screen, for example a text field highlighted in color. The determined human body part may also be visually highlighted and may be illuminated for good visibility.

According to an embodiment, in the event of detection of an object, an evaluation of further predetermined articles is made and when an article of this kind is determined in the beam path, a further signal, different from the signal or the display for a body part, or a further display is output. Such articles may be for example instruments, scissors or hoses or holding mechanisms, that may be adversely affected by irradiation or constitute a danger themselves.

For carrying out the method a monitoring system is provided, that is associated with an X-ray apparatus controlled by a system controller with an X-ray source designed for emitting an X-ray, including a monitoring unit that may be triggered by the system controller, configured for continuous scanning of a first three-dimensional volume for objects; an evaluation unit, configured for evaluation of objects detected by the monitoring unit as to whether the object is a human body part that does not correspond to the examination object; and an output unit for outputting a signal or a display.

BRIEF DESCRIPTION OF THE FIGURES

FIG. 3 depicts a flowchart of a method according to an embodiment.

FIG. 4 depicts a flowchart of a method according to an embodiment.

DETAILED DESCRIPTION

Figure 1:
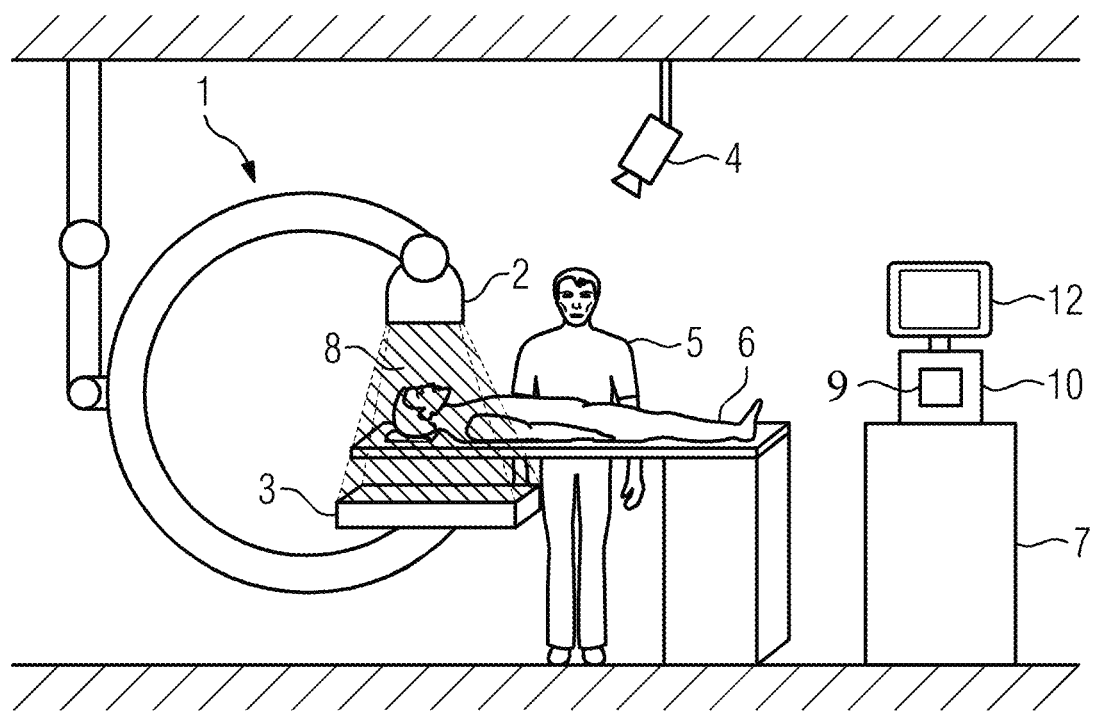
FIG. 1 depicts a view of an X-ray apparatus including a monitoring system according to an embodiment.
Figure 2:
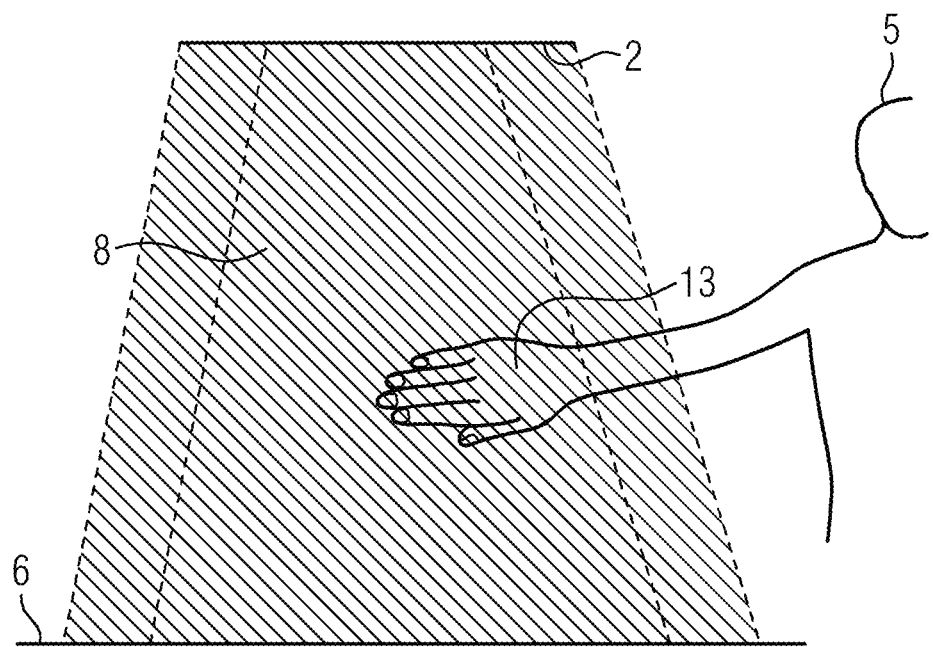
FIG. 2 depicts a view of an object in the volume irradiated by the X-ray beam according to an embodiment.

FIG. 1 depicts an X-ray apparatus 1, with a monitoring system associated with the X-ray apparatus 1. The X-ray apparatus 1 includes a C-arm with an X-ray source 2 arranged at one end and an X-ray detector 3 arranged at the other end, with the X-ray source configured for emitting an X-ray beam. After X-raying an examination object (e.g. an organ of a patient 6) arranged on an examination table, the X-ray beam strikes the X-ray detector 3. A collimator (not shown) is provided for shaping the X-ray. The X-ray apparatus is controlled by a system controller 7. Medical personnel 5, such as, for example doctors or nurses, are in the space with the X-ray apparatus. If, for example under X-ray control by the medical personnel, an operative or interventional procedure is carried out, there is a danger of a body part or several body parts, for example hands or arms, of one or more person(s) of the medical personnel being located in the beam path of the X-ray for a relatively long time and being irradiated with undesirable X-ray radiation. This is depicted, for example, in FIG. 2 where a hand 13 of a person of the medical personnel 5 is located in a first three-dimensional volume 8 directly irradiated by the X-ray beam of the X-ray apparatus 1. To prevent this, a monitoring system is associated with the X-ray apparatus, and includes at least one monitoring unit (depicted in the form of a 3D camera 4); a control unit 10; an evaluation unit 9 and an output unit (depicted in the form of a display unit 12). The X-ray irradiation occurs for example during the course of an interventional procedure such as the introduction of a catheter or the insertion of an implant (for example stent) or an endovascular aneurysm repair (EVAR), something that is performed under X-ray control to be able to monitor exact positioning better.

FIG. 3 depicts a flowchart of a method. The monitoring unit is activated at act 22 that may occur routinely at any time to provide continuous monitoring, or in conjunction with an envisaged or planned procedure. Activation of the monitoring unit may be connected with activation of the X-ray source (see FIG. 4) or occur independently thereof. The monitoring unit may be for example one or more 3D camera(s) 4, that is capable of monitoring three-dimensional volumes. Other monitoring units may also be used, for example infrared equipment or terahertz cameras. The first three-dimensional volume, that monitors the monitoring unit, may be chosen and adjusted in advance, for example by a user of the system or automatically by the system controller. The monitored first three-dimensional volume 8 includes the domain directly irradiated by X-ray radiation. A second three-dimensional volume may be provided and monitored that includes regions affected by scatter radiation. The monitoring unit (therefore, for example 3D camera 4) may be mounted for example at a point on the ceiling or wall of the space in which the X-ray apparatus is located or may also be arranged on the examination table or for example the C-arm. A good view of the monitoring unit onto the first three-dimensional volume penetrated by radiation is possible.

Once the monitoring unit is activated, the monitoring unit remains so at least until the irradiation by the X-ray source is ended. The monitoring unit may also be operated continuously or for example as long as people remain in the affected space. If an object is detected in the volume during monitoring by the monitoring unit at act 23, the object is then checked at act 24—for example by the evaluation unit 9—for whether, firstly, it is a human body part and, secondly, whether the human body part is a human body part that does not correspond to the examination object. The evaluation may be performed for example by an algorithm of a computer vision method, in other words for example on the basis of an object recognition method or an edge recognition method. Adaptive neural networks may be used here, moreover, to progressively improve the recognition of human body parts.

For the case where a human body part is detected during evaluation that does not correspond to the examination object, a signal is generated, or a display is output at act 25 to inform the medical personnel. Therefore, for example a warning tone or a warning light may be output or for example the human body part may be illuminated in color. A text display may also be output on a screen or a mobile device. The optical or acoustic signals may be sent to devices specifically configured, for example to the pager of the relevant doctor or to a projector installed in the space. The signal may also be formed by a haptic signal. The medical personnel are immediately alerted to the danger, so the affected human body part may quickly be removed from the danger zone.

In addition to the signal or the display, the collimator of the X-ray apparatus may be configured in such a way that the human body part is shielded from the direct X-ray radiation or the dose is at least partially reduced. A finger filter may be pushed into the beam path of the X-ray, controlled for example by the system controller of the X-ray apparatus. In the case where the dose is reduced by a filter (not completely shielded), an adjusted image enhancement may be carried out for the part-shielded image region to achieve a brightness that is constant over the entire acquired image. In this way X-ray imaging of acceptable quality is also still possible for the part-shielded image region.

The first three-dimensional volume 8 may be automatically specified as a function of the beam path of the X-ray. Information about the beam path (for example the collimation, etc.) may be passed by the system controller of the X-ray apparatus to the control unit of the monitoring unit and used for this purpose. Information about the region irradiated by the X-ray beam is continuously renewed for timely monitoring and the first three-dimensional volume 8 continuously adjusted accordingly.

In addition to monitoring of the human body parts, an evaluation of predetermined articles may also take place in the case of detection of an object. When an article of this kind is determined in the beam path, a further signal, different from the signal or the display for a body part, or a further display may be output. Such articles may be for example instruments, scissors or hoses or holding mechanisms, that may be adversely affected by irradiation or constitute a danger themselves.

FIG. 4 depicts further acts that may take place before act 22. The X-ray source 2 of the X-ray apparatus 1 may be activated at act 20 to emit X-ray radiation that then penetrates the examination object and then strikes the X-ray detector. In a manner timely with activation of the X-ray source 2, a trigger signal is transmitted to the monitoring system in a sixth step 21 (for example wirelessly or by a cable connection), whereby the monitoring unit is activated in act 22.

Medical personnel, for example, in the case of operative or interventional procedures under X-ray monitoring, are made aware of the dangers quickly and simply by direct (and indirect) X-ray radiation and health risks may therefore be permanently reduced.

Embodiments includes a method for monitoring the exposure to radiation of medical personnel during an X-ray examination of an examination object with an X-ray apparatus, including the following steps: activation of a monitoring unit. The monitoring unit continuously scans a first three-dimensional volume, that includes a region directly irradiated by the X-ray beam, for objects. In the event of detection of an object, automatic evaluation as to whether the object is a human body part that does not correspond to the examination object, and outputting of a signal or a display if a human body part is determined inside the first three-dimensional volume that does not correspond to the examination object.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for monitoring the exposure to radiation of medical personnel during an X-ray examination of an examination object with an X-ray apparatus, the method comprising:

activating a monitoring unit, wherein activating of the monitoring unit is triggered by an activation of an X-ray source that emits an X-ray beam;

scanning, continuously by the monitoring unit a first three-dimensional volume that comprises a region that is irradiated by the X-ray beam, for objects;

detecting an object;

evaluating whether the object is a human body part that does not correspond to the examination object; and outputting a signal or a display when a human body part is determined inside the three-dimensional volume that does not correspond to the examination object.

2. The method of claim 1, wherein the first three-dimensional volume is automatically specified as a function of a beam path of the X-ray beam.

3. The method of claim 1, wherein the monitoring unit comprises at least one 3D camera, an infrared device, or a terahertz camera.

4. The method of claim 1, wherein evaluating is performed using computer vision.

5. The method of claim 1, further comprising:

renewing information about the region irradiated by the X-ray beam; and adjusting the first three-dimensional volume as a function of the information.

6. The method of claim 1, wherein evaluating is performed using one or more neural networks.

7. The method of claim 1, further comprising:

scanning, by the monitoring unit, a second three-dimensional volume that comprises a region affected by scatter radiation, for one or more objects;

evaluating whether the one or more objects is a human body part that does not correspond to the examination object; and outputting a signal when the human body part is determined inside the second three-dimensional volume that does not correspond to the examination object.

8. The method of claim 1, furthering comprising:

adjusting when a human body part is determined inside the first three-dimensional volume, a collimation of the X-ray of the X-ray source.

9. The method of claim 8, wherein the collimation changes the region irradiated by the X-ray beam so that the human body part is no longer irradiated.

10. The method of claim 1, wherein the signal is formed by an optical or acoustic or haptic signal.

11. The method of claim 1, wherein the determined human body part is optically highlighted in the display.

12. The method of claim 1, further comprising:

evaluating, after detection of an object, further predetermined articles; and outputting a second signal or display different from the signal and the display.

13. A monitoring system comprising:

an X-ray apparatus comprising:

an X-ray source configured to emit an X-ray beam;

a system controller configured to control the X-ray source;

a monitoring unit triggered by an activation of the X-ray source that emits the X-ray beam, the monitoring unit configured to continuous scan a first three-dimensional volume for objects;

an evaluation unit configured to evaluate objects detected by the monitoring unit and determine whether the object is a human body part that does not correspond to an examination object; and an output unit configured to output a signal or a display when the object is a human body part that does not correspond to an examination object.

14. The monitoring system of claim 13, wherein the first three-dimensional volume is automatically specified as a function of a beam path of the X-ray beam.

15. The monitoring system of claim 13, wherein the monitoring unit comprises at least one 3D camera, an infrared device, or a terahertz camera.

16. The monitoring system of claim 13, wherein the evaluation unit is configured to evaluate objects using computer vision.

17. The monitoring system of claim 13, wherein the evaluation unit is configured to evaluate objects using one or more neural networks.

18. The monitoring system of claim 13, wherein the determined human body part is optically highlighted by the output unit in the display.

* * * * *